(12) United States Patent
Dobrowolski

(10) Patent No.: US 9,435,716 B2
(45) Date of Patent: Sep. 6, 2016

(54) FORENSIC COLLECTION DEVICE

(71) Applicant: VIBOD GMBH, Radebeul (DE)

(72) Inventor: Peter Dobrowolski, Radebeul (DE)

(73) Assignee: VIBOD GMBH, Radebeul (DE)

( * ) Notice: Subject to any disclaimer, the term of this patent is extended or adjusted under 35 U.S.C. 154(b) by 206 days.

(21) Appl. No.: 14/351,986

(22) PCT Filed: Oct. 19, 2012

(86) PCT No.: PCT/EP2012/070748
§ 371 (c)(1),
(2) Date: Apr. 15, 2014

(87) PCT Pub. No.: WO2013/057245
PCT Pub. Date: Apr. 25, 2013

(65) Prior Publication Data
US 2015/0007671 A1    Jan. 8, 2015

(30) Foreign Application Priority Data

Oct. 21, 2011    (EP) ..................... 11186238

(51) Int. Cl.
*G01N 1/02*    (2006.01)
*A61B 10/00*    (2006.01)

(52) U.S. Cl.
CPC ............. *G01N 1/02* (2013.01); *A61B 10/0045* (2013.01); *G01N 2001/028* (2013.01)

(58) Field of Classification Search
CPC ........................................... G01N 1/02
USPC ....................................... 73/864.51
See application file for complete search history.

(56) References Cited

U.S. PATENT DOCUMENTS

| 5,988,002 | A | 11/1999 | Danylewych-May et al. |
| 2005/0252820 | A1 | 11/2005 | Sanchez-Felix et al. |
| 2007/0270713 | A1* | 11/2007 | Ng ..................... A61B 10/0045 600/570 |
| 2008/0058676 | A1* | 3/2008 | Yong .................. A61B 10/0051 600/572 |
| 2009/0209044 | A1 | 8/2009 | Gallagher et al. |

FOREIGN PATENT DOCUMENTS

EP    1 022 554    7/2000

OTHER PUBLICATIONS

International Search Report issued in International Application No. PCT/EP2012/070748 on Dec. 12, 2013.

* cited by examiner

*Primary Examiner* — Lisa Caputo
*Assistant Examiner* — Jamel Williams
(74) *Attorney, Agent, or Firm* — Ballard Spahr LLP

(57) ABSTRACT

The present invention discloses a device as well as a collection element (1) for collecting a chemical and/or biological sample directly from a surface exposing said sample material. Furthermore, a method for collecting a chemical and/or biological sample directly from a surface exposing said sample material and a kit thereof is subject-matter of the present invention.

24 Claims, 2 Drawing Sheets

D

C

B

A

FORENSIC COLLECTION DEVICE

Figure 1:
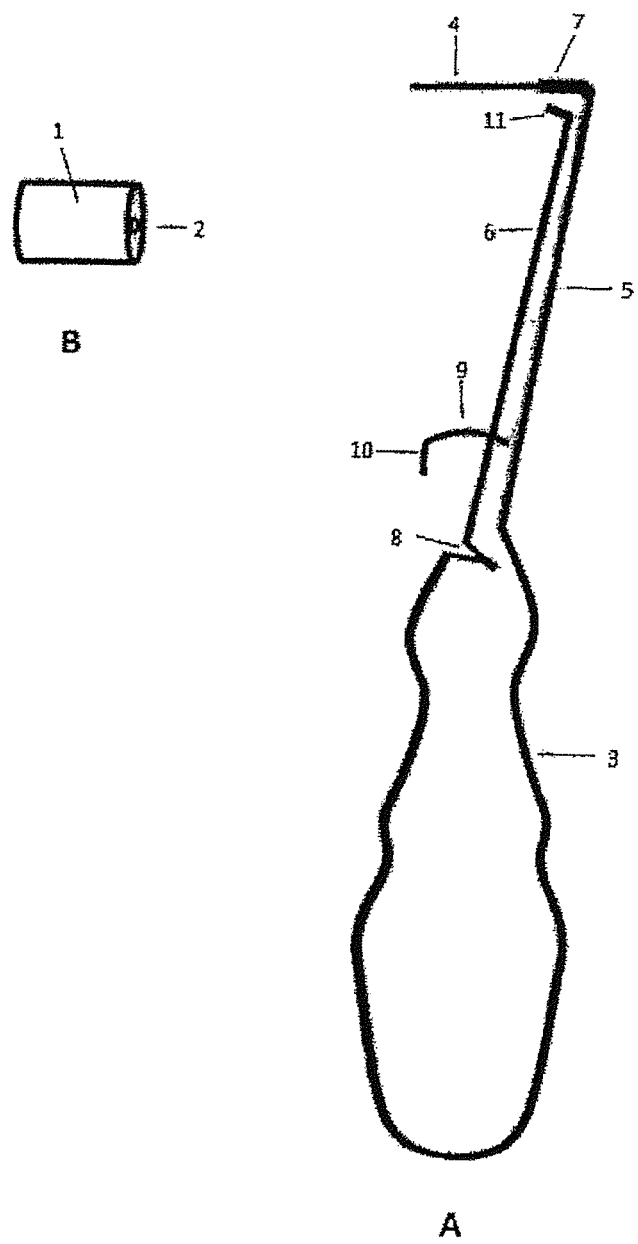

This application is a U.S. National Stage Application of PCT International Patent Application No. PCT/EP2012/070748, which was filed on Oct. 19, 2012, which claims priority to European Patent. Application No. 11186238.9 filed Oct. 21, 2011, the disclosure of each of which is incorporated herein by reference in its entirety.

FIELD OF THE INVENTION

The present invention relates to the field of chemical and biological sample preparation, particularly the present invention relates to devices for isolation of samples, particularly of chemical and biological samples.

BACKGROUND OF THE INVENTION

The various fields of forensic expertise include for example toxicology, serology and DNA profiling, trace evidence (e.g. fire debris, glass, paint, gunshot residues), firearms and ballistics, handwriting and document examination, fingerprints, marks and impressions (e.g. tool marks, shoe prints), audio, video and computer analysis, accident investigation, crime scene investigation and forensic pathology. Particularly, the analysis of biological and chemical material has long been of paramount importance in forensic investigations.

Recent technological advances have broadened the scope of such investigations by facilitating analysis of tiny amounts of samples which is called trace evidence and includes the analysis of hair, touched surfaces, fiber, paint, glass, soil, and other particulate matter such as samples containing nucleic acids and proteins. The analysis of DNA from cells by molecular biological methods, such as PCR (polymerase chain reaction), RFLP (restriction fragment length polymorphism), AFLP (amplified fragment length polymorphism) or sequencing permits, for example, the detection of genetic defects or the determination of the HLA (human leukocyte antigen) type as well as other genetic markers, like short tandem repeats (STR) for the identification of individuals.

As the benefits of being able to analyse certain components of biological samples, for example nucleic acids or proteins, have become known, and as the analyses themselves have become more accurate and more accessible, such analyses have become important and frequently used tools, available not only to the medical and veterinary professions, but also in a wide range of other areas, such as in the analysis of forensic materials, pharmaceutical products and intermediates, foods and environmental materials. In many of these areas it is important to maintain the integrity of the molecular structure of a sample while strictly avoiding the contamination and loss of sample.

Responding to a crime scene is a critical step in the scientific investigation of a case. Unless the crime scene response is handled correctly, the investigation may be severely compromised. Crime Scene investigators and crime scene specialists are responsible for identifying, securing, collecting, and preserving evidence which is submitted to the crime laboratory. The investigator's knowledge in crime scene documentation and the variety of methods for the collection and processing of all types of evidence is crucial.

Current procedures for the collection and/or handling of biological and chemical samples employ solid matrices such as cellulose- or cotton-based papers or swabs. After the visual identification the solid matrix is pressed on the surface on which the sample is expected to accept ideally all of the sample material. Adhesion of the sample material is enhanced by different means depending on the structure of the surface on which the sample is to be collected. Same applications prefer the moistening of the solid matrix. Other applications make use of a solid matrix coated with glue, i.e. an adhesive tape. The latter is particularly preferred when the surface is structured, e.g. textiles, due to a higher adhesive force. Another advantage of an adhesive tape is that the sample is not wetted and can be stored dry. Samples collected with a moistened matrix are to be dried before storage to prevent from disintegration such as chemical or biological degradation and to prevent moulding.

The use of an adhesive tape requires a well grounded person. When applying an adhesive tape for the collection of a forensic sample one has to trim the tape according to the desired length using scissors or a knife. The middle part of the tape is used for collecting the sample and the two side parts are used to manually handle the tape. After collecting the sample, the side parts should be cut off saving the middle part for further processing. In order to avoid (cross-) contamination, sterile gloves, scissors and knifes must be changed every time after a single sample has been collected. This procedure is difficult to implement at a crime scene, in any case cumbersome and, thus, bears a high risk for contamination. Furthermore, the flexibility of the tape which is advantageous for the collection from non-even surfaces leads to the undesired sticking of parts of the glued surface to other parts of the tape or to the inner wall surface of a sample tube which is used in the further processing of the sample. This can hamper the subsequent release of the sample from the tape significantly, e.g. when incubating the adhesive tape with lysis buffer to release DNA.

Some disadvantages could be overcome by a development of Helling GmbH (Heidgraben) which offers a device for sample collection which consists of a rod and a rigid or an elastic element at one end of the rod. A double-sided adhesive tape is attached to said element which can be then used to sweep a surface on which a sample is expected. Such devices are called tape lift stubs. Afterwards the double-sided adhesive tape is removed manually or with the aid of a forceps from the element and put into a sample tube. Though this development omitted the cutting of the tape, there are still a significant number of steps which require the touching of the tape by hands or by other external means. Furthermore, the glued surface is limited according to its construction, e.g. 6.6 and 12.7 $mm^2$ as published in Verheil et al. and DeBruin et al. (Forensic Sci. Int., 2011, A protocol for direct and rapid multiplex PCR amplification on forensically relevant samples; Forensic Sci. Int., 2011, Comparison of stubbing and the double swab method for collecting offender epithelial material from a victims skin).

Further devices are known from U.S. 2009/0252820 and U.S. 2009/0209044. These devices employ a sampling head which is detachable from the handle. The detachment mechanism is based on a physical disintegration of the device, i.e. the sampling head is irreversibly torn off the handle. The detachment mechanism bears the risk of cross-contamination when absorbed material bespatters around once the sampling head abruptly tears off. A further disadvantage can be seen in that it is not possible to re-use the handle or, in case of the device according to U.S. 2009/0209044, re-use it without dissembling the whole device, which is not feasible at a crime scene.

A re-use, in turn, appears to be feasible with a device disclosed in U.S. Pat. No. 5,988,002. However, the sampling element is here to be manually grasped taking care not to contact the working portion. Application errors will certainly end in cross-contamination.

In summary, current methods and devices for sample collection from solid surfaces are cumbersome, inefficient, prone to (cross-) contamination and can lead to loss of sample material.

The handling of trace evidence is of particular challenge. Trace evidence is usually not or only hardly visible. The rather big adhesion force makes it sticky towards all kind of surfaces which hampers the handling, e.g. the transfer of the sample from a collection device into a sample tube. As trace evidence is present in tiny quantities, contamination produces a high background even in very small amounts. For example, foreign DNA may completely distort the result of DNA profiling. Due to the above disadvantages, none of the current procedures appear to be useful for handling trace evidence.

Accordingly, it is an object of the present invention to provide a device for collecting a biological and/or chemical sample from a surface exposing said sample material without the above outlined drawbacks.

DESCRIPTION OF THE INVENTION

The problem is solved through the provision of a device for collecting a forensic biological and/or chemical sample directly from a surface exposing said sample material comprising (i) a holding element (5) comprising a plug (4) at a first end, (ii) a releasing element (6) connected to the holding element (5) and (iii) a collection element (1) comprising, on the lateral area of the collection element (1), a collection surface on which said sample is deposited and at least one side surface, wherein the plug extends into the collection element along or parallel to the longitudinal axis of the collection element, wherein the collection element (1) is attached in a mechanically detachable fashion to the holding element (5), and wherein the releasing element (6) is capable of exerting a mechanical force to the side surface of the collection element such that the collection element (5).

The problem is further solved by the present invention through the provision of a device for collecting a biological and/or chemical sample directly from a surface exposing said sample material comprising (i) a holding element (5), (ii) a releasing element (6) and (iii) a collection element (1) on which said biological sample is deposited, wherein the collection element (1) is attached in a mechanically detachable fashion to the holding element (5), and wherein the releasing element (6) is capable of mechanically detaching the collection element (1) from the holding element (5).

The present invention also provides for a collection element (1) for the above device.

The present invention further provides for a device comprising a holding element (5) and a releasing element (6) for the above device.

The present invention further provides for a kit for collecting a biological and/or chemical sample directly from the biological source comprising the above device and a closable sample tube sized and shaped to accept the collection element (1).

The present invention further provides for a method for collecting a biological and/or a chemical sample directly from a surface exposing said sample material comprising contacting the biological sample with the above collection element (1).

FIGURE LEGEND

The following Figures are enclosed herein to exemplify preferred embodiments of the present invention. They shall in no way be interpreted as narrowing the scope of the present invention.

FIG. 1: A: Preferred device comprising a holding element (5) and a releasing element (6). Attached to the releasing element (6) is a lever (10) which when actuated moves the top end (11) of the releasing element (6) in the direction of the mounting (4) at which the collection element (1) is fastened and pushes the collection element (1) off the mounting. The flexibility is obtained by a slip tongue joint (8), which acts like a forceps. The mounting (4) shown is either thinner than the holding element (5) which forms a thickening (7) such that the collection element (1) is secured against lateral shifting. Holding element (5) and releasing element (6) are connected to a handhold (3). B: Preferred collection element (1) having a cylindrical shape and designed to be pivot-mounted when fastened to the holding element (5).

Figure 2:
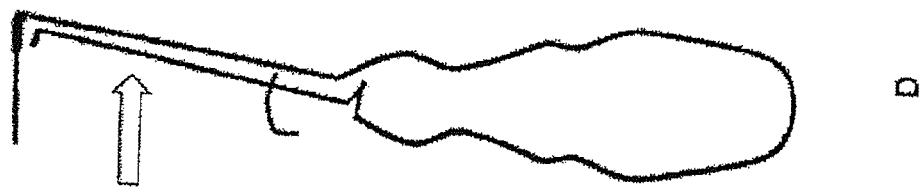
Figure 2:
Figure 2:
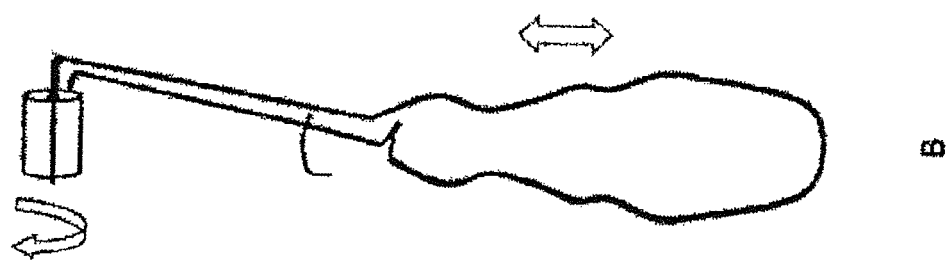
Figure 2:
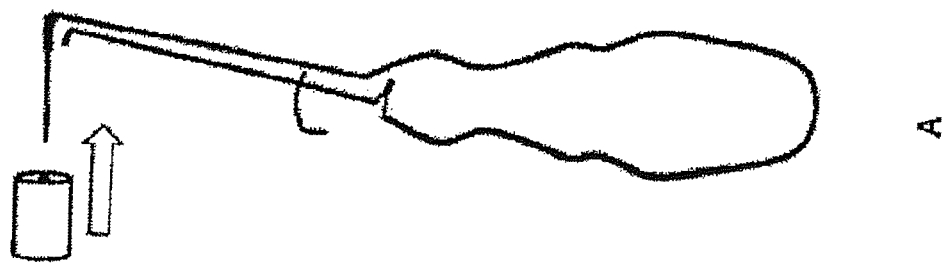

FIG. 2: Release mechanism of a preferred embodiment of the herein disclosed device.

DETAILED DESCRIPTION OF THE INVENTION

The term "forensic chemical or biological sample" is interchangeably used with a "forensic sample". It herein refers to any kind of chemical or biological substance or substance mixture of forensic interest.

Such forensic samples include blood, sputum, saliva, semen, urine, hair, or other appropriate fluid or tissue from personal items (e.g. toothbrush, razor, etc).

Furthermore, so-called trace evidence is included which means evidence that occurs when different objects contact one another. Such materials are often transferred by contact friction. Examples of typical trace evidence include both chemical and biological samples such as fingerprints, hairs, cosmetics, plant fibers, mineral fibers, synthetic fibers, glass, paint chips, soils, botanical materials, gunshot residue, explosives residue, and volatile hydrocarbons (arson evidence). For such evidence to be useful, it must be compared to similar items from suspects, but particular care is necessary to ensure a thorough analysis.

In a preferred embodiment the forensic sample comprises (an) isolated cell(s) or (a) nucleic acid(s). The term "nucleic acid" is here used in its broadest sense and comprises ribonucleic acids (RNA) and deoxyribonucleic acids (DNA) from all possible sources, in all lengths and configurations, such as double-stranded, single-stranded, circular, linear or branched. All sub-units and sub-types are also comprised, such as monomeric nucleotides, oligomers, plasmids, viral and bacterial nucleic acids, as well as genomic and non-genomic DNA and RNA from animal and plant cells or other eukaryotes or prokaryotes, messenger RNA (mRNA) in processed and unprocessed form, transfer RNA (tRNA), heterogeneous nuclear RNA (hn-RNA), ribosomal RNA (rRNA), complementary DNA (cDNA) as well as all other conceivable nucleic acids.

The device (as well as the kit and method described below) is particularly suited for but not limited to the collection of forensic samples. As such, it is useful for collecting samples for food or environmental analysis and the like. Such samples include in addition to those mentioned above microorganisms (e.g. viruses, bacteria, fungi), impurities (e.g. heavy metals, side products), and the like.

The device for collecting a (e.g. forensic) biological and/or chemical sample directly from a surface exposing said sample material comprises (i) a holding element (5), (ii) a releasing element (6) and (ii) a collection element (1) on which said biological sample is deposited, wherein the collection element (1) is attached in a mechanically detachable fashion to the holding element (5), and wherein the releasing element (6) is capable of mechanically detaching the collection element (1) from the holding element (5).

Alternatively, the device for collecting a forensic biological and/or chemical sample directly from a surface exposing said sample material comprises (i) a holding element (5) comprising a plug (4) at a first end, (ii) a releasing element (6) connected to the holding element (5) and (iii) a collection element (1) comprising, on the lateral area of the collection element (1), a collection surface on which said sample is deposited and at least one side surface, wherein the plug extends into the collection element (1) along or parallel to the longitudinal axis of the collection element (1), wherein the collection element (1) is attached in a mechanically detachable fashion to the holding element (5), and wherein the releasing element (6) is capable of exerting a mechanical force to the side surface of the collection element such that the collection element (5).

Collecting a sample directly from a surface is understood to describe the fact that said collection element (1) has been used directly during the collection of the sample, i.e. that said collection element (1) is brought in close contact with said biological sample, e.g. by rubbing over a surface on which the sample is expected. Non-direct collection in contrast would be if another collection device was used for collecting the biological sample and the biological sample would have been then deposed by that collection device on the collection element (1) according to the invention, e.g. by washing it from said collection device on the collection element (1).

From the features of the device it becomes apparent that, after use, the collection element (1) can be detached from the holding element (5) and subsequently a new collection element (1) may be mounted on the plug (4) of the holding element (5) for re-using the device. In other words, the detachment mechanism can be understood to be adapted to facilitate a reversible detachment of the collection element (1). In this context, it is preferred that the collection element (1) and the holding element (5) are attached to each other via a plug-and-socket connection.

Preferably, the second end of the holding element (5) and the releasing element (6) are connected directly to each other or via a handhold (3). The connection may be based on glue, cement, friction, positive locking, and so on. A handhold (3) herein means a part or thing to take hold of. The handhold (3) may have varying shapes as the skilled person is aware of. Preferred is an ergonomically shaped handhold (3), such as a bar-like shape.

The holding element (5), the releasing element (6) and the handhold (3) form the frame of the device. Preferably, the holding element (5), the releasing element (6) and the handhold (3) are integral. Preferably, the frame is made of the same material, for example a (e.g. metal) wire, or plastic. Though, for ease of preparation, the frame are made of the same plastic, also a combination of different plastics may be convenient depending on the desired properties of the respective elements. Most preferably, the frame is manufactured in a one-shot molding process. A metal wire may be prepared by forming by bending. A plastic device may be made by injection molding.

The holding element (5) is shaped and sized such that the collection element (1) can be attached to one end, i.e. to a mounting (4). Depending on the shape of the collection element (1) it is preferred that the collection element (1) is vertically aligned or aligned parallel with the holding element (5). For example, the holding element (5) may be L-, Z- or U-shaped. A non-limiting example of a holding element (5) is shown in FIG. 1. Any attachment is possible as long as it is possible to disconnect the attachment using the releasing element (6). The attachment is preferably based on friction. The mounting (4) is preferably thinner than the holding element (5) or the holding element (5) has a thickening (7) such that the collection element (1) is secured against lateral shifting. In a preferred embodiment, the collection element is reversibly attached to the holding element (5)/to the plug (4) of the holding element (5).

It is preferred that the collection surface is perpendicular to the handhold (3) as illustrated in FIGS. 1 and 2.

It is further preferred that the collection element (1) and the holding element (5) are attached to each other via a plug-and-socket connection. In this case, the collection element (1) preferably comprises the socket and the holding element (5) preferably comprises the plug (4), or vice versa.

The releasing element (6) is sized and shaped such that it releases the collection element (1) from the holding element (5) when said release is levered. A lever (10) is preferably integral with the releasing element (6) and located such that it can be actuated with the same hand which holds the device, i.e. that the device can be operated with only one hand. The releasing element (6) is moveable such that the lever (10) can be moved in the direction of the collection element (1) to push the collection element (1) off the holding element (5). When no pressure is exercised onto the lever (10), the flexible releasing element (6) returns into its initial position. In a preferred embodiment the releasing element (6) is only partly flexible, e.g. has a slip tongue joint (8), which acts like a forceps.

The holding element (5) and the releasing element (6) are attached to a handhold (3) which is preferably ergonomically designed to fit into a human hand. It is conceivable that the handhold (3) has a rod-like shape like a shaft of a hammer or preferably like a shaft of a screw driver. A non-limiting example of such design is shown in FIG. 1. It is also conceivable that the holding element (5), the releasing element (6) and the handhold (3) are integral. Preferably, the device is sized and shaped such that the releasing element can be actuated with the same hand which holds the device.

The collection element (1) can have different shapes and sizes depending on the needs. It can be spherical, cylindrical or conical, which is particular preferred when the collection element (1) is pivot-mounted which can be obtained by an axial borehole (2) in the collection element (1) and a spindle/plug (4) at the holding element (5). A pivot-mounted collection element (1) is capable of sampling large areas in a rather short time. Hence, many applications will make it desirable to have a pivot-mounted collection element (1). If the collection element (1) is not pivot-mounted, it can also be rectangular, square, or which is considered to be suitable by the skilled person. As will be understood by the skilled person, the size of the collection element (1) depends on the area of the surface to be sampled. Alike, the texture of the collection element (1) depends on the texture of the surface to be sampled as well as whether the sample is solid or liquid. The collection element (1) may consist of various materials. The skilled person will readily appreciate that the material may be selected according to the desired properties with respect to the stiffness and/or reactivity with the liquids and/or solids. He will furthermore recognize that it is preferred that the materials do not interact with liquids (e.g. extraction and/or lysis buffers) and/or solids of the samples to be analyzed. Furthermore, the material may be selected to withstand buffers and chemicals used in procedures of incubation and/or isolation of chemical and/or biological samples. In an alternative embodiment, it is desired that the collection element is of a material which is solid in a dry state and dissolvable when wetted, e.g. with a solution of water or a particular fluid, as described in WO-A1 2008/080932. Upon addition of the solution, a part or the entire collection element is dissolved and the sample is released into the solution.

If the adhesive strength is to be increased, the collection element (1) is preferably coated with adhesive. Either all or part of the collection element (1) can be coated. If it is spherical, cylindrical or conical it is preferred that the curved surface area is coated with adhesive. If the collection element (1) is rectangular or the like, it may be sufficient to have only one side coated with adhesive. Depending on the desired adhesive strength different adhesives can be used. For example, adhesives having a higher strength, e.g. acrylate based adhesives, are desired when textiles are to be sampled, paper surfaces are preferably sampled with adhesives of a lower strength, e.g. pressure sensitive adhesives based on rubber.

In many cases, the sample is to be collected from structured surfaces, such as textiles, small items, such as pencils and complex instruments with sections of small surfaces, like telephones. The accessibility to such surfaces is difficult and the recovery often low. Hence, in a preferred embodiment the collection element (1) is of an elastic material to compensate the unevenness of a surface from which the sample is to be collected. Examples of such materials are polypropylene and foamed rubber which do no absorb liquid.

The isolation of sample material from a collection device is usually done with a liquid. An excess of liquid is to be avoided, particularly when dealing with trace evidence, since the concentration of the compounds to be analyzed, e.g. nucleic acids, may be diluted below the detection limit. Hence, the collection element (1) of the invention is preferably of a material which hardly absorbs liquids. More preferably, the collection element (1) is of a non-absorbent material. However, if the sample to be analyzed is a liquid, it can be desirable to have a collection element (1) comprising a non-absorbent core and a liquid-absorbent surface. Desirable characteristics with respect to absorbance and desorption have flocked materials. Since sample and processing tubes are most often cylindrical, a collection element (1) which is cylindrical or spherical and has a diameter just a little bit smaller than the diameter of the tube has the advantage that the required amount of isolation/extraction liquid is small.

The isolation and/or further processing is performed in a conventional sample tube or processing tubes which are particular designed for this purpose. Such processing tube is for example described in GB-A 2 139 519 or is for example available as PrepFiler LySep™ column (Applied Biosystems). Hence, the collection element (1) is sized and shaped to fit in a sample collection tube and/or a sample processing tube. The dimensions of the collection element (1) may be adapted depending on the needs. However, since the laboratory equipment, e.g. centrifuges in chemical, medical, biological and forensic laboratories as well as sample and processing tubes are often standardized; the dimensions of the collection element (1) are chosen to be compatible with standard laboratory equipment.

If the collection element (1) is cylindrical it is preferred that the outer diameter is between 5.5 and 6 mm and/or the length is between 10 and 11 mm and/or the surface area or adhered area is between 1.73 and 2.07 $cm^2$. If the collection element (1) is spherical it is preferred that the outer diameter is between 5.5 and 6 mm and/or the surface area or adhered area is between 0.95 and 1.13 $cm^2$.

If the collection element (1) is coated with adhesive it is preferred that it is a pressure sensitive adhesive, for example an adhesive based on rubber, resin, silicone, acrylate, methacrylate or a composition thereof. For an easy collection it is desired that the pressure sensitive adhesive has an adhesive strength adjusted to enable low-friction motion on the surface from which the sample is to be collected.

As will be readily understood by the skilled person, the device or at least the collection element (1) should be properly treated, e.g. with ethylene dioxide or gamma radiation, and packaged such that it is sterile and DNA-free before use. It is further conceivable that, particularly if the collection element (1) is coated with adhesive, the collection element (1) and/or the adhesive surface is wrapped to protect the adhesive. Therefore, waxed paper, silicone paper, a foil and/or a combination thereof can be used as a wrap.

The holding element (5) and the releasing element (6) are preferably re-usable but can be also single-use. More important is that the collection element (1) is single-use. Said elements and the handhold (3) may be made of plastic or metal and are stiff with the exception of the flexible part of the releasing element (8).

The invention is directed to the above device. Also embraced is a collection element (1) for the above device as described herein as well as a device comprising a holding element (5) and a releasing element (6) for the above device, i.e. the above device without the collection element (1), i.e. a device for collecting a biological and/or chemical sample directly from a surface exposing said sample material comprising (i) a holding element (5) and (ii) a releasing element (6), wherein the holding element (5) is sized and shaped that a collection element (1) can be attached in a mechanically detachable fashion, and wherein the releasing element (6) is capable of mechanically detaching the collection element (1) from the holding element (5).

Furthermore, a kit for collecting a (e.g. forensic) biological and/or chemical sample directly from the biological source comprising the above device and a closable sample tube sized and shaped to accept the collection element (1) is embraced by the present invention. It is conceivable that the kit further comprises a packaging and a seal for sealing the packaging and/or sample tube. It is also conceivable that the packaging and/or the sample tube has means for labelling.

A method for collecting a (e.g. forensic) biological and/or a chemical sample directly from a surface exposing said sample material comprising contacting the biological sample with the collection element (1) of the above device is further embraced by the present invention. The method may further comprise detaching the collection element (1) into a sample tube sized and shaped to accept the collection element (1). Preferably, the detaching is effected by the releasing element (6).

The invention claimed is:
1. A device, which can be used with one hand, for collecting a forensic biological and/or chemical sample directly from a surface exposing said sample material comprising:

(i) a holding element (5) comprising a plug (4) at a first end, (ii) a releasing element (6) connected to the holding element (5) and (iii) a collection element (1) comprising, on the lateral area of the collection element (1), a collection surface on which said sample is deposited and at least one side surface, wherein the plug extends into the collection element (1) along or parallel to the longitudinal axis of the collection element (1), wherein the collection element (1) is attached in a mechanically detachable fashion to the holding element (5), and wherein the releasing element (6) is capable of exerting a mechanical force to the side surface of the collection element (1) such that the collection element (1) is detached from the holding element (5), wherein the second end of the holding element (5) and the releasing element (6) are connected directly to each other or are connected via a handhold (3), and wherein the holding element (5), the releasing element (6) and the handhold (3) are integral.

2. The device according to claim 1, wherein the holding element (5) is L-, Z- or U-shaped.

3. The device according to claim 1, wherein the collection surface is perpendicular to the handhold (3).

4. The device according to claim 1, wherein the collection element (1) and the holding element (5) are attached to each other via a plug-and-socket connection, wherein the collection element (1) comprises the socket and the holding element (5) comprises the plug (4).

5. The device according to claim 1, wherein the device is sized and shaped such that the releasing element can be actuated with the same hand which holds the device.

6. The device according to claim 1, wherein the collection element (1) has a cylindrical or spherical shape.

7. The device according to claim 1, wherein the collection element (1) is pivot-mounted.

8. The device according to claim 1, wherein the collection element (1) is of an elastic material to compensate the unevenness of a surface from which the sample is to be collected.

9. The device according to claim 1, wherein the collection element (1) is of a non-absorbent material.

10. The device according to claim 1, wherein the collection element (1) is sized and shaped to fit in a sample collection tube and/or a sample processing tube.

11. The device according to claim 1, wherein the collection element (1) is coated with adhesive.

12. The device according to claim 11, wherein the adhesive is a pressure sensitive adhesive.

13. The device according to claim 12, wherein the pressure sensitive adhesive is an adhesive based on rubber, resin, silicone, acrylate, methacrylate or a composition thereof.

14. The device according to claim 12, wherein the pressure sensitive adhesive has an adhesive strength adjusted to enable low-friction motion on the surface from which the sample is to be collected.

15. The device according to claim 11, wherein the collection element (1) and/or the adhesive is wrapped to protect the adhesive.

16. The device according to claim 15, wherein the wrap is waxed paper, silicone paper, a foil and/or a combination thereof.

17. The device according to claim 1, wherein the holding element (5) and the releasing element (6) are reusable and/or wherein the collection element (1) is single-use.

18. A kit for collecting a biological and/or chemical sample directly from a surface exposing said sample material comprising the device according to claim 1 and a closable sample tube sized and shaped to accept the collection element (1).

19. The kit according to claim 18 further comprising a packaging and a seal for sealing the packaging and/or sample tube, optionally wherein the packaging and/or the sample tube has means for labelling.

20. A method for collecting a biological and/or a chemical sample directly from a surface exposing said sample material comprising contacting the biological sample with the collection element (1) of the device according to claim 1.

21. The method according to claim 20 further comprising detaching the collection element (1) into a sample tube sized and shaped to accept the collection element (1).

22. The method according to claim 20, wherein the detaching is effected by actuating the releasing element (6).

23. The device according to claim 6, wherein the collection element (1) has a cylindrical shape, wherein the cylindrical collection element (1) has an outer diameter between 5.5 mm and 6 mm.

24. The device according to claim 23, wherein the cylindrical collection element (1) has a length between 10 mm and 11 mm.

* * * * *